United States Patent [19]

Janssens

[11] 4,167,574

[45] Sep. 11, 1979

[54] N-PHENYL-N-(4-PIPERIDINYL)AMIDES

[75] Inventor: Frans Janssens, Putte, Belgium

[73] Assignee: Janssen Pharmaceutica, N.V., Belgium

[21] Appl. No.: 954,709

[22] Filed: Oct. 25, 1978

Related U.S. Application Data

[63] Continuation-in-part of Ser. No. 886,188, Mar. 13, 1978, abandoned, which is a continuation-in-part of Ser. No. 793,814, May 5, 1977, abandoned.

[51] Int. Cl.$^2$ ............... C07D 401/06; A61K 31/445
[52] U.S. Cl. .................................. 424/267; 546/194; 546/210; 546/223; 424/263; 546/224; 546/212; 548/251

[58] Field of Search ............... 546/194, 210; 424/267, 424/263

[56] References Cited

U.S. PATENT DOCUMENTS 3,998,834  12/1976  Janssen et al. ............... 260/293.68

Primary Examiner—John M. Ford
Assistant Examiner—Robert T. Bond
Attorney, Agent, or Firm—Salvatore R. Conte

[57] ABSTRACT

Novel compounds of the series of N-phenyl-N-(4-piperidinyl)amides having a (4,5-dihydro-4-R-5-oxo-1H-tetrazol-1-yl)alkyl or (4,5-dihydro-4-R-5-thioxo-1H-tetrazol-1-yl)alkyl substituent group in the 1-position of the piperidine nucleus, said compounds being useful as analgesic agents.

14 Claims, No Drawings

N-PHENYL-N-(4-PIPERIDINYL)AMIDES

CROSS-REFERENCE TO RELATED APPLICATIONS:

This is a continuation-in-part of my copending application, Ser. No. 886,188, filed Mar. 13, 1978, now abandoned which in turn is a continuation-in-part of parent application Ser. No. 793,814, filed May 5, 1977, now abandoned.

BACKGROUND OF THE INVENTION:

In U.S. Pat. No. 3,998,834 there are described a number of N-phenyl-N-(4-piperidinyl)amides having analgesic properties. The compounds of this invention differ from the foregoing essentially by the nature of the (4,5-dihydro-4-R-5-oxo-1H-tetrazol-1-yl)alkyl or (4,5-dihydro-4-R-5-thioxo-1H-tetrazol-1-yl)alkyl group present in the 1-position of the piperidine nucleus.

DESCRIPTION OF THE PREFERRED EMBODIMENTS:

This invention is concerned with novel N-phenyl-N-(4-piperidinyl)amides which may be represented by the structural formula:

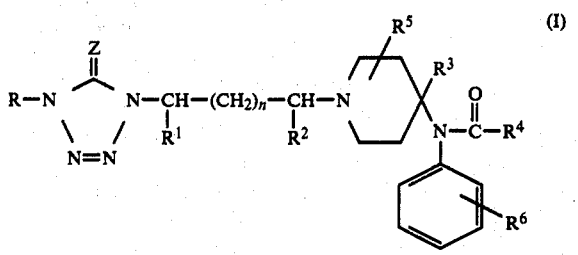

and the pharmaceutically acceptable acid addition salt thereof, wherein:

R is a member selected from the group consisting of hydrogen, lower alkyl, cycloalkyl, lower alkenyl, lower alkynyl, (lower alkyl)-oxy(lower alkyl), aryl and aryl(lower alkyl);

$R^1$ is a member selected from the group consisting of hydrogen, lower alkyl and aryl;

$R^2$ is a member selected from the group consisting of hydrogen and lower alkyl;

$R^3$ is a member selected from the group consisting of lower alkyloxycarbonyl, lower alkyloxymethyl and lower alkylcarbonyl;

$R^4$ is a member selected from the group consisting of lower alkyl, cycloalkyl, lower alkenyl, lower alkyloxy and arylmethyl;

$R^5$ is a member selected from the group consisting of hydrogen and lower alkyl;

$R^6$ is a member selected from the group consisting of hydrogen, halo, lower alkyl, lower alkyloxy and trifluoromethyl;

Z is a member selected from the group consisting of O and S; and n is the integer 0 or 1;

wherein said aryl as used in the foregoing definitions is selected from the group consisting of phenyl, substituted phenyl, thienyl and pyridinyl, said substituted phenyl having from 1 to 2 substituents independently selected from the group consisting of halo, lower alkyl, lower alkyloxy and trifluoromethyl.

The term "lower alkyl" as used herein is meant to include straight and branch chained alkyl radicals having from 1 to 6 carbon atoms, such as, for example, methyl, ethyl, 1-methylethyl, 1,1-dimethylethyl, propyl, butyl, pentyl, hexyl and the like; the term "cycloalkyl" refers to cycloalkyl radicals having from 3 to 6 carbon atoms, e.g., cyclopropyl, cyclobutyl, cyclopentyl and cyclohexyl; "lower alkenyl" refers to alkenyl radicals having from 3 to 6 carbon atoms such as, for example, 2-propenyl, 2-butenyl, 3-pentenyl, 2-hexenyl and the like; and lower alkynyl refers to alkynyl radicals having from 3 to 6 carbon atoms such as, for example, 2-propynyl, 2-butynyl and the like.

The compounds of formula (I) wherein Z is O, (I-a), can generally be prepared by the reaction of a 4,5-dihydro-1H-tetrazol-5-one derivative of the formula

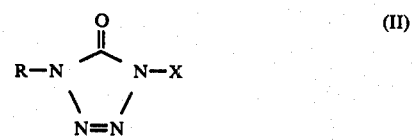

with a N-phenyl-N-(4-piperidinyl)amide of the formula

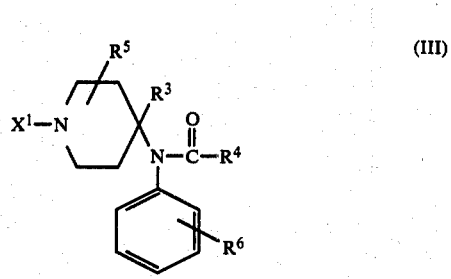

wherein R, $R^3$, $R^4$, $R^5$ and $R^6$ are as above-defined and either $X^1$ is hydrogen and X is a radical of the formula

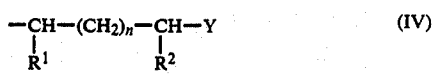

or X is hydrogen and $X^1$ is a radical of the formula

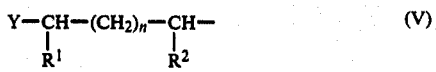

In the above formulae (IV) and (V) $R^1$, $R^2$ and n have the previously indicated meaning and Y is a reactive ester residue, such as, for example, halo, more particularly chloro, bromo or iodo, or a sulfonyloxy group, such as, for example, methylsulfonyloxy or 4-methylphenylsulfonyloxy.

The reaction of (II) with (III) may be carried out following standard N-alkylating procedures as generally known in the art. Said reaction is advantageously conducted in an appropriate, reaction-inert organic solvent, such as, for example, an aromatic hydrocarbon, e.g., benzene, methylbenzene, dimethylbenzene and the like; a lower alkanol, e.g., methanol, ethanol, 2-propanol, 1-butanol and the like; a ketone, e.g., 4-methyl-2-pentanone and the like; an ether, e.g., 1,4-dioxane, 1,1'-oxybisethane and the like; N,N-dimethylformamide; nitrobenzene; and the like. The addition to the reaction mixture of an appropriate base, such as, for example, an alkali metal carbonate or hydrogen carbonate, or an organic base, such as, for example, N,N-diethylethanamine or N-(1-methylethyl)-2-propanamine may be utilized to pick up the acid that is liberated during the course of the reaction. In some cases the addition of an iodide salt, preferably an alkali metal iodide, is appropriate. Somewhat elevated temperatures are advantageously employed to enhance the reaction rate. In some circumstances, especially when one of the substituents $R^1$ and $R^2$ is methyl and the other is hydrogen, a partial rearrangement may occur during the reaction yielding a mixture of position isomers wherein respectively $R^1$ is methyl and $R^2$ is hydrogen and inversely $R^1$ is hydrogen and $R^2$ is methyl. Such position isomers can easily be separated from each other by known isolation techniques such as, for example, selective crystallisation from an appropriate solvent system or column-chromatography.

The compounds of formula (I-a) can also be prepared by acylating an appropriate 4-piperidinamine of the formula

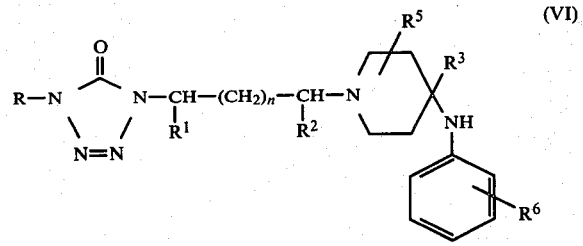

Said acylation reaction is conveniently carried out according to known N-acylation procedures, for example, by reacting (VI) with an appropriate acyl halide, $R^4$-CO-halo, representing respectively a lower alkylcarbonyl halide, a cycloalkylcarbonyl halide, an arylacetyl halide or a lower alkyl carbonohalidate, following methodologies known in the art. When $R^4$ represents lower alkyl or cycloalkyl the acylation may also be carried out with an anhydride derived from the acid $R^4COOH$.

The compounds of formula (I) wherein Z is S, (I-b), can generally be derived from the corresponding (I-a) by reacting the latter with an appropriate sulfurating agent such as, for example, $P_2S_5$. The reaction may be conveniently carried out by stirring and heating the reactants together in an appropriate reaction-inert organic solvent such as, for example, an aromatic hydrocarbon such as, benzene, methylbenzene, dimethylbenzene and the like.

The compounds of formula (I) wherein R represents hydrogen are preferably derived from the corresponding (I) wherein R represents phenylmethyl by debenzylating the latter in the usual manner, e.g., by catalytic hydrogenation using an appropriate catalyst such as palladium-on-charcoal.

In the foregoing and subsequent preparations, the reaction products are isolated from the reaction mixture, and, if necessary, further purified by the application of common isolation and purification procedures as generally known in the art.

A number of the compounds within the scope of formula (I) have one or more asymmetric carbon atoms within their structure and consequently exist under different stereochemically isomeric forms. More particularly when $R^1$ or $R^2$ are other than hydrogen, the carbon atoms to which they are attached are asymmetric, while additional asymmetric carbon atoms may be present in the lower alkyl groups comprised in R, $R^3$ and $R^4$. While in the above preparations there are obtained essentially mixtures, including racemic mixtures of such stereochemical isomers, such mixtures can generally be resolved into their stereochemically pure isomeric forms by the application of known resolution techniques, e.g., by salt formation with optical isomers of asymmetric acids and selective crystallisation of the salts thus obtained. The stereochemically isomeric forms of compounds of formula (I) are included within the scope of formula (I).

As a result of their basic properties, the compounds of formula (I) can be converted to their therapeutically active, non-toxic acid addition salt form by treatment with an appropriate acid, such as, for example, an inorganic acid, such as hydrohalic acid, e.g., hydrochloric, hydrobromic, and the like, and sulfuric acid, nitric acid, phosphoric acid and the like; or an organic acid, such as, for example, acetic, propanoic, hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, α-hydroxybenzoic, 4-amino-2-hydroxybenzoic and the like acids. Conversely, the salt form can be converted by treatment with alkali into the free base form.

The starting materials of formula (II) wherein X is hydrogen, (II-a), can easily be prepared by the reaction of an appropriate isocyanate of the formula (VII) or an acylchloride of the formula (VII') with sodium azide in the presence of aluminium chloride in an appropriate organic solvent, preferably an ether such as tetrahydrofuran (THF).

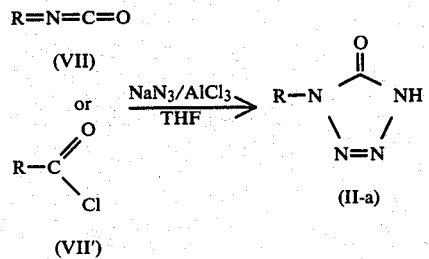

The reaction is conveniently carried out by stirring and heating the reactants together in the solvent for several hours. When an acyl chloride of formula (VII) is used as a reactant at least 2 molar equivalents of the azide have to be employed and the use of an additional excess thereof is generally found appropriate.

Starting materials of formula (II) wherein X is a radical of the formula (IV), (II-b), can be obtained by introducing said radical into the corresponding (II-a) by known methods.

In general, said starting materials (II-b) can be prepared by carrying out the steps of:

(i) reacting the appropriate (II-a) with a haloalkanol derivative of the formula

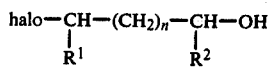 (VIII)

following generally known N-alkylating procedures as previously described herein, to obtain an intermediate of the formula

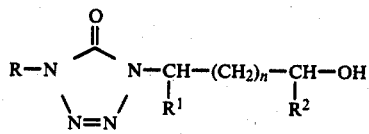 (IX)

and;

(ii) subsequently converting the hydroxy group of the thus obtained (IX) into a reactive ester group following art-known procedures of preparing reactive esters starting from the corresponding alcohols.

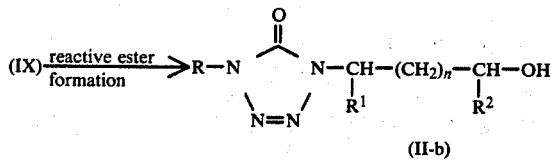
(II-b)

Halides are conveniently obtained by the reaction of (IX) with an appropriate halogenating agent, such as, for example, sulfinyl chloride, sulfuryl chloride, phosphor pentachloride, phosphor pentabromide, phosporyl chloride and the like. When the reactive ester is an iodide, it is preferably derived from the corresponding chloride or bromide by the replacement of that halogen with iodine. Reactive sulfonate esters such as methanesulfonates and 4-methylbenzenesulfonates are conveniently prepared by reacting the alcohol with an appropriate sulfonyl halide such as, for example, methanesulfonyl chloride and 4-methylbenzenesulfonyl chloride respectively.

When Y in (II-b) is chloro, (II-b-1), the introduction of the chloroalkyl chain can also be performed by the reaction of an appropriate (II-a) with an appropriate bromo-chloroalkane derivative of the formula (X) following standard N-alkylating procedures to obtain the corresponding (II-b-1).

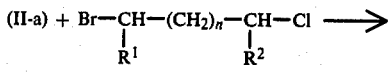
(X)

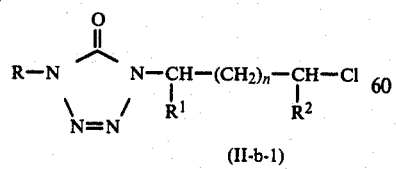
(II-b-1)

Alternatively, the starting materials (II-b-1) wherein R is other than hydrogen or phenyl can be obtained by introducing the R-substituent into a precursor of the formula

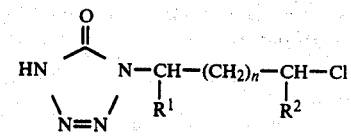 (XI)

Said introduction of R is conveniently carried out by the reaction of (XI) with an appropriate reactive ester RY wherein R is as previously defined but other than hydrogen or phenyl, following standard N-alkylating procedures as described hereinabove. It is to be noted that when said Y in said RY is iodo, the chloro substituent of (XI) may be replaced during the reaction by iodo, especially when an excess of the alkylating iodide is employed. The precursor compounds of formula (XI) may be prepared following the procedures described in Tetrahedron, 31, 765 (1975) wherein the compound of formula (XI) wherein $R^1$ and $R^2$ are both hydrogen and n is 1 is specifically described.

The starting materials of formula (III) wherein $X^1$ is hydrogen, (III-a), can be prepared according to the procedures outlined in U.S. Pat. No. 3,998,834 wherein a number of such starting materials and their preparation are described.

The starting materials of formula (III) wherein $X^1$ is a radical of the formula (V), (III-b), can be prepared by N-alkylating a piperidine derivative of the formula (III-a) with a haloalkanol of the formula (XII) in the usual manner to obtain an intermediate of the formula (XIII) and thereafter converting the hydroxy group of the latter into a reactive ester group as previously described.

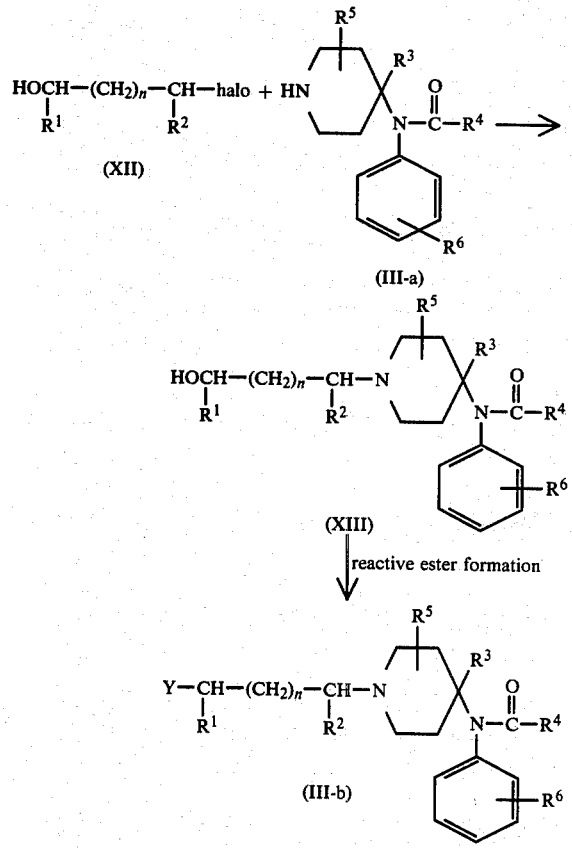

Intermediates of formula (XIII) herein wherein n is 0 can also be obtained by the reaction of (III-a) with an appropriately substituted oxirane of the formula

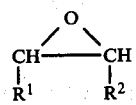

It is to be noted that when in formula (XIV) one of the radicals $R^1$ and $R^2$ is methyl, the other being hydrogen, there is substantially obtained an intermediate (XIII) wherein the methyl substituent is located at the β-position with respect to the piperidine nitrogen. Intermediates of formula (XIII) wherein $R^1$ is phenyl and n is zero and methods of preparing them are also described in U.S. Pat. No. 3,998,834.

The reaction of (XIV) with (III-a) is conveniently carried out by stirring and heating the reactants together in an appropriate organic solvent, such as, for example, an aromatic hydrocarbon, e.g., benzene, methylbenzene, dimethylbenzene, and the like; a halogenated hydrocarbon, e.g., dichloromethane and trichloromethane; or a lower alkanol, e.g., methanol, ethanol, 2-propanol and the like; and preferably in a mixture of an aromatic hydrocarbon and a lower alkanol. The reaction may be promoted by the addition of an appropriate base, such as, for example, an alkali metal carbonate or hydrogen carbonate.

Starting materials of formula (III-b) wherein Y is chloro (III-b-1), can also be prepared directly by the reaction of (III-a) with a bromo-chloroalkane of the formula (XV) following methods similar to those described herein for the preparation of starting materials (II-b-1) starting from (II-a).

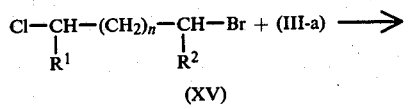

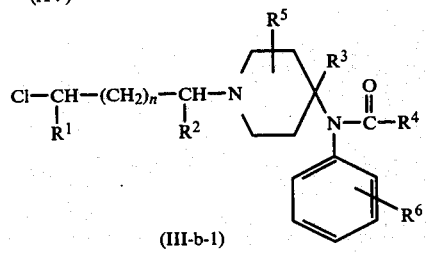

The starting materials of formula (VI) herein can generally be prepared by the reaction of a reactive ester of the formula (II) wherein R represents a radical of the formula (IV) with a 4-piperidinamine of the formula

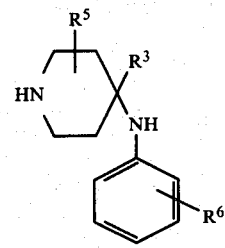

following similar procedures as described herein for the preparation of the compounds (I-a) starting from (II) and (III).

The 4-piperidinamines of formula (XVI) used as starting materials herein can also be prepared following the procedures described in U.S. Pat. No. 3,998,834 wherein a number of such compounds are specifically described.

The ultimate starting materials in each of the above procedures are generally known and they may all be prepared following art-known procedures as are described in the literature for preparing such known compounds.

The compounds of formula (I) and the pharmaceutically acceptable acid addition salts thereof have very interesting pharmacological properties. More particularly they are potent morphine-like analgesics and as such they can be used to depress pain in warm-blooded animals.

The useful analgesic properties of the compounds of formula (I) and acid addition salts thereof are clearly evidenced by the results obtained in the rat tail withdrawal test, described in Arzneimittel-Forschung, 13, 502 (1963) and 21, 862 (1971).

The results in the table I below indicate the LED, i.e. the lowest 100% effective dose in mg/kg upon intravenous administration, and the duration (expressed in minutes) of this effect at the stated dose.

Table I

| R | $R^1$ | $R^2$ | $R^3$ | $R^4$ | Base or Salt form | LED in mg/kg s.c. | duration in min. |
|---|---|---|---|---|---|---|---|
| CH₃ | CH₂—CH₂ | | COOCH₃ | C₂H₅ | (COOH)₂ | 0.16 | 39 |
| C₂H₅ | CH₂—CH₂ | | COOCH₃ | C₂H₅ | 1 1/2(COOH)₂ | 0.16 | 19 |
| nC₃H₇ | CH₂—CH₂ | | COOCH₃ | C₂H₅ | (COOH)₂ | 0.16 | 11 |
| iC₃H₇ | CH₂—CH₂ | | COOCH₃ | C₂H₅ | (COOH)₂ | 2.5 | 41 |

Table I-continued

| R | CH—(CH$_2$)$_n$—CH<br>R$^1$  R$^2$ | R$^3$ | R$^4$ | Base or Salt form | LED in mg/kg s.c. | duration in min. |
|---|---|---|---|---|---|---|
| tC$_4$H$_9$ | CH$_2$—CH$_2$ | COOCH$_3$ | C$_2$H$_5$ | (COOH)$_2$ | 2.5 | 18 |
| nC$_5$H$_{11}$ | CH$_2$—CH$_2$ | COOCH$_3$ | C$_2$H$_5$ | (COOH)$_2$ | 2.5 | 20 |
|  | CH$_2$—CH$_2$ | COOCH$_3$ | C$_2$H$_5$ | (COOH)$_2$ | <0.63 | 150 |
| ⟨H⟩ | CH$_2$—CH$_2$ | COOCH$_3$ | C$_2$H$_5$ | (COOH)$_2$ | ≧10 | 45 |
| CH$_3$ | CH$_2$—CH$_2$ | CH$_2$OCH$_3$ | C$_2$H$_5$ | (COOH)$_2$ | 0.16 | 31 |
| C$_2$H$_5$ | CH$_2$—CH$_2$ | CH$_2$OCH$_3$ | C$_2$H$_5$ | HCl . H$_2$O | 0.08 | 17 |
| iC$_3$H$_7$ | CH$_2$—CH$_2$ | CH$_2$OCH$_3$ | C$_2$H$_5$ | HNO$_3$ . H$_2$O | 0.63 | 12 |
| C$_2$H$_5$ | CH$_2$—CH(CH$_3$) | CH$_2$OCH$_3$ | C$_2$H$_5$ | HNO$_3$ | 0.16 | 13 |
| C$_6$H$_5$ | CH$_2$—CH(CH$_3$) | CH$_2$OCH$_3$ | C$_2$H$_5$ | HNO$_3$ | 10 | 14 |
| C$_2$H$_5$ | CH$_2$—CH$_2$—CH$_2$ | CH$_2$OCH$_3$ | C$_2$H$_5$ | HCl ½H$_2$O | 2.5 | 14 |

A preferred group of compounds within the scope of formula (I) is represented by those wherein R is a lower alkyl radical. In fact these preferred compounds are highly potent analgesics having a short duration of action. Analgesics having such a short duration of action are highly desirable in circumstances where acute severe pain has to be eliminated over a short period, e.g., in anaesthesiology.

In view of their analgesic activity, the subject compounds may be formulated into various pharmaceutical forms for administration purposes. To prepare the pharmaceutical compositions of this invention, an effective analgesic amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, preferably, for administration orally, rectally or by parenteral injection. For example, in preparing the compostions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of the analgesic activity of the subject compounds, it is evident that the present invention provides a method of preventing or combatting pain in warm-blooded animals, by the systemic administration of an effective analgesic amount of a compound of formula (I) or a pharmaceutically acceptable acid addition salt thereof in admixture with a pharmaceutical carrier. Although the amount of active ingredient to be administered may vary within rather wide limits, depending on the particular circumstances of the case, doses of from about 0.01 mg/kg to about 1 mg/kg, administered once or repeatedly are generally found effective.

The following examples are intended to illustrate and not to limit the scope of the present invention. Unless otherwise stated all parts therein are by weight.

EXAMPLE I

To a stirred mixture of 14.2 parts of isocyanatoethane, 29.2 parts of sodium azide and 135 parts of dry tetrahydrofuran is added a solution of 39 parts of aluminium chloride in 225 parts of dry tetrahydrofuran. Stirring is continued overnight at reflux temperature.

The reaction mixture is cooled and acidified with a hydrochloric acid solution 6 N. The whole is evaporated to dry and the product is extracted four times with 2-propanone. The combined extracts are dried, filtered and evaporated. The residue is dried overnight, yielding 18 parts (65%) of 1-ethyl-1,4-dihydro-5H-tetrazol-5-one.

EXAMPLE II

Following the procedure of Example I and using an equivalent amount of respectively isocyanatocyclohexane and 2-isocyanatopropane as a starting material there are obtained:

1-cyclohexyl-1,4-dihydro-5H-tetrazol-5-one; and
1,4-dihydro-1-(1-methylethyl)-5H-tetrazol-5-one as a residue.

EXAMPLE III

To 990 parts of tetrahydrofuran, cooled in an ice-bath, are added portionwise 156 parts of aluminium chloride and the whole is stirred vigorously till all solid enters solution. This solution is added quickly to a stirred suspension of 208 parts of sodium azide in 225 parts of tetrahydrofuran and stirring is continued for 1 hour at reflux temperature. After cooling to room temperature, there is added dropwise a solution of 54 parts of butanoyl chloride in 225 parts of tetrahydrofuran at a temperature below 30° C. The whole is heated slowly to reflux and stirring is continued overnight at reflux temperature. While cooling, the reaction mixture is acidified with 800 parts of a hydrochloric acid solution 6 N and the solvent is evaporated. The residue is stirred in a sodium hydrogen carbonate solution, trichloromethane is added and the layers are separated. The aqueous phase is acidified with concentrated hydrochloric acid and the solvent is evaporated. The residue is stirred in 2-propanone. The precipitate is filtered off and the filtrate is evaporated, yielding 32 parts of 1,4-dihydro-1-propyl-5H-tetrazol-5-one as a residue.

EXAMPLE IV

Following the procedure of Example III and using an equivalent amount of an appropriate acyl chloride as a starting material, the following compounds are obtained:

1-(1,1-dimethylethyl)-1,4-dihydro-5H-tetrazol-5-one as a residue;
1,4-dihydro-1-pentyl-5H-tetrazol-5-one;
1,4-dihydro-1-(2-phenylethyl)-5H-tetrazol-5-one as a solid residue;
1,4-dihydro-1-(phenylmethyl)-5H-tetrazol-5-one; mp. 152° C.; and
1-cyclopropyl-1,4-dihydro-5H-tetrazol-5-one; mp. 128° C.

EXAMPLE V

A mixture of 22 parts of 1-ethyl-1,4-dihydro-5H-tetrazol-5-one, 45 parts of 1-bromo-2-chloroethane, 26 parts of sodium carbonate, 0.3 parts of potassium iodide and 240 parts of 4-methyl-2-pentanone is stirred and refluxed overnight with water-separator. The reaction mixture is cooled, water is added and the layers are separated. The aqueous phase is extracted three times with dichloromethane. The combined organic phases are dried, filtered and evaporated. The residue is purified by column-chromatography over silica gel using trichloromethane as eluent. The pure fractions are collected and the eluent is evaporated, yielding 28.4 parts (80%) of 1-(2-chloroethyl)-4-ethyl-1,4-dihydro-5H-tetrazol-5-one as a residue.

EXAMPLE VI

Following the procedure of Example V and using equivalent amounts of respectively an appropriate 1,4-dihydro-5H-tetrazol-5-one and an appropriate bromochloroalkane as starting materials the following 1-(chloroalkyl)-1,4-dihydro-5H-tetrazol-5-ones are obtained:

1-(2-chloroethyl)-1,4-dihydro-4-propyl-5H-tetrazol-5-one as a residue;
1-(2-chloroethyl)-1,4-dihydro-4-(1-methylethyl)-5H-tetrazol-5-one as a residue;
1-(2-chloroethyl)-4-(1,1-dimethylethyl)-1,4-dihydro-5H-tetrazol-5-one as a residue;
1-(2-chloroethyl)-1,4-dihydro-4-pentyl-5H-tetrazol-5-one as a residue;
1-(2-chloroethyl)-4-cyclohexyl-1,4-dihydro-5H-tetrazol-5-one as a residue;
1-(2-chloroethyl)-1,4-dihydro-4-(2-phenylethyl)-5H-tetrazol-5-one as a residue;
1-(3-chloropropyl)-4-ethyl-1,4-dihydro-5H-tetrazol-5-one as a residue;
1-(2-chloroethyl)-1,4-dihydro-4-(phenylmethyl)-5H-tetrazol-5-one as a residue; and
1-(2-chloroethyl)-4-cyclopropyl-1,4-dihydro-5H-tetrazol-5-one as a residue.

EXAMPLE VII

A mixture of 49 parts of iodomethane, 10.5 parts of 1-(2-chloroethyl)-1,4-dihydro-5H-tetrazol-5-one, 15 parts of sodium carbonate, 0.2 parts of potassium iodide and 240 parts of 4-methyl-2-pentanone is stirred and refluxed overnight with water-separator. The reaction mixture is cooled, 100 parts of water are added and the layers are separated. The aqueous phase is extracted with dichloromethane. The combined organic phases are dried, filtered and evaporated. The residue is purified by column-chromatography over silica gel using trichloromethane as eluent. The pure fractions are collected and the eluent is evaporated, yielding 15 parts (85%) of 1,4-dihydro-1-(2-iodoethyl)-4-methyl-5H-tetrazol-5-one as a residue.

EXAMPLE VIII

A mixture of 19.6 parts of [2-(2-thienyl)ethyl] 4-methylbenzenesulfonate, 10 parts of 1-(2-chloroethyl)-1,4-dihydro-5H-tetrazol-5-one, 10 parts of sodium carbonate and 90 parts of N,N-dimethylformamide is stirred and heated overnight at 70° C. The reaction mixture is cooled, 100 parts of water are added and the product is extracted three times with methylbenzene. The combined extracts are dried, filtered and evaporated. The residue is purified by column-chromatography over silica gel using a mixture of trichloromethane and petroleumether (70:30 by volume) as eluent. The pure fractions are collected and the eluent is evaporated, yielding 15 parts (46.5%) of 1-(2-chloroethyl)-1,4-dihydro-4-[2-(2-thienyl)ethyl]-5H-tetrazol-5-one as a residue.

EXAMPLE IX

To 4.5 parts of sulfinyl chloride is added dropwise a mixture of 13 parts of N-[1-(2-hydroxy-2-phenylethyl)-4-(methoxymethyl)-4-piperidinyl]-N-phenylpropanamide hydrochloride and 260 parts of dichloromethane. Upon completion, the whole is stirred and refluxed for a few hours. The reaction mixture is cooled and the solvent is evaporated. The residue is taken up in 2-propanone. The mixture is filtered and the filtrate is treated with activated charcoal. The latter is filtered off and the filtrate is evaporated. The residue is crystallized from a mixture of 2-propanone and 2,2'-oxybispropane. The product is filtered off and dried, yielding 9.2 parts (61.7%) of N-[1-(2-chloro-2-phenylethyl)-4-(methoxymethyl)-4-piperidinyl]-N-phenylpropanamide monohydrochloride; mp. 145.3° C.

EXAMPLE X

A mixture of 35 parts of 2-methyloxirane, 83 parts of N-[4-(methoxymethyl)-4-piperidinyl]-N-phenylpropanamide, 25 parts of sodium hydrogen carbonate, 450 parts of benzene and 80 parts of methanol is stirred and refluxed overnight. The reaction mixture is evaporated and the residue is taken up in water. The product is extracted with trichloromethane. The extract is dried, filtered and evaporated. The residue is converted into the hydrochloride salt in 2-propanol. The salt is filtered off and crystallized from a mixture of 2,2'-oxybispropane and 2-propanol, yielding 41.5 parts (37%) of N-[1-(2-hydroxypropyl)-4-(methoxymethyl)-4-piperidinyl]-N-phenylpropanamide monohydrochloride.

14 Parts of sulfinyl chloride are stirred and there is added dropwise a solution of 37 parts of N-[1-(2-hydroxypropyl)-4-(methoxymethyl)-4-piperidinyl]-N-phenylpropanamide monohydrochloride in 360 parts of dichloromethane. Upon completion, stirring is continued overnight at reflux temperature. The reaction mixture is evaporated and the residue is suspended in 2-propanone. The product is filtered off and dried, yielding 31.5 parts (85%) of N-[1-(2-chloropropyl)-4-(methoxymethyl)-4-piperidinyl]-N-phenylpropanamide monohydrochloride.

EXAMPLE XI

A mixture of 1.8 parts of 1-(2-chloroethyl)-4-ethyl-1,4-dihydro-5H-tetrazol-5-one, 3.45 parts of N-[4-(methoxymethyl)-4-piperidinyl]-N-phenylpropanamide, 5 parts of sodium carbonate, 0.2 parts of potassium iodide and 240 parts of 4-methyl-2-pentanone is stirred and refluxed overnight with water-separator. The reaction mixture is poured onto water and the layers are separated. The organic phase is dried, filtered and evaporated. The residue is purified by column-chromatography over silica gel using a mixture of trichloromethane and methanol (97:3 by volume) as eluent. The pure fractions are collected and the eluent is evaporated. The residue is converted into the hydrochloride salt in 2-propanone. The salt is filtered off and crystallized from 2-propanone, yielding 1.5 parts (33.3%) of N-{1-[2-(4-ethyl-4,5-dihydro-5-oxo-1H-tetrazol-1-yl)ethyl]-4-(methoxymethyl)-4-piperidinyl}-N-phenylpropanamide monohydrochloride monohydrate; mp. 140.8° C.

EXAMPLE XII

Following the procedure of Example XI and using equivalent amounts of the appropriate starting materials, the following compounds are obtained as acid addition salts after treatment of the free base form with an appropriate acid:

N-{1-[2-(4,5-dihydro-5-oxo-4-propyl-1H-tetrazol-1-yl)ethyl]-4-(methoxymethyl)-4-piperidinyl}-N-phenylpropanamide ethanedioate (1:2) monohydrate; mp. 103.8° C.

N-[1-{2-[4,5-dihydro-(1-methylethyl)-5-oxo-1H-tetrazol-1-yl]-ethyl}-4-(methoxymethyl)-4-piperidinyl]-N-phenylpropanamide mononitrate monohydrate; mp. 104.5° C.

methyl 1-[2-{4,5-dihydro-5-oxo-4-[2-(2-thienyl)ethyl]-1H-tetrazol-1-yl}ethyl]-4-[(1-oxopropyl)-phenylamino]-4-piperidinecarboxylate ethanedioate (1:1) mp. 162.9° C.;

N-{1-[3-(4-ethyl-4,5-dihydro-5-oxo-1H-tetrazol-1-yl)propyl]-4-(methoxymethyl)-4-piperidinyl}-N-phenylpropanamide hydrochloride hemihydrate; mp. 182° C.; and N-[1-{2-[4,5-dihydro-5-oxo-4-(phenylmethyl)-1H-tetrazol-1-yl]-ethyl}-4-(methoxymethyl)-4-piperidinyl]-N-phenylpropanamide ethanedioate (1:1); mp. 166.4° C.

EXAMPLE XIII

A mixture of 3.6 parts of 1-(2-chloroethyl)-4-ethyl-1,4-dihydro-5H-tetrazol-5-one, 6.4 parts of methyl 4-[N-(1-oxopropyl)N-phenylamino]-4-piperidinecarboxylate hydrochloride, 4 parts of sodium carbonate, 0.1 parts of potassium iodide and 240 parts of 4-methyl-2-pentanone is stirred and refluxed overnight with water-separator. The reaction mixture is cooled and poured onto water. The organic phase is separated, dried, filtered and evaporated. The residue is purified by column-chromatography over silica gel using a mixture of trichloromethane and methanol (97:3 by volume) as eluent. The pure fractions are collected and the eluent is evaporated. The residue is converted into the ethanedioate salt in 2-propanone. The salt is filtered off and dried, yielding 1.5 parts (13%) of methyl 1-[2-(4-ethyl-4,5-dihydro-5-oxo-1H-tetrazol-1-yl)ethyl]-4-[(1-oxopropyl)phenylamino]-4-piperidinecarboxylate ethanedioate (2:3); mp. 158.9° C.

EXAMPLE XIV

Following the procedure of Example XIII and using equivalent amounts of the appropriate starting materials, the following ethanedioate salts are obtained:

methyl 1-[2-(4,5-dihydro-5-oxo-4-propyl-1H-tetrazol-1-yl)ethyl]-4-[(1-oxopropyl)phenylamino]-4-piperidinecarboxylate ethanedioate (1:1); mp. 168.4° C.;

methyl 1-{2-[4,5-dihydro-4-(1-methylethyl)-5-oxo-1H-tetrazol-1-yl]ethyl}-4-[(1-oxopropyl)phenylamino]-4-piperidinecarboxylate ethanedioate (1:1); mp. 184.2° C.;

methyl 1-{2-[4-(1,1-dimethylethyl)-4,5-dihydro-5-oxo-1H-tetrazol-1-yl]ethyl}-4-[(1-oxopropyl)phenylamino]-4-piperidinecarboxylate ethanedioate (1:1); mp. 168.1° C.;

methyl 1-[2-(4,5-dihydro-5-oxo-4-pentyl-1H-tetrazol-1-yl)ethyl]-4-[(1-oxopropyl)phenylamino]-4-piperidinecarboxylate ethanedioate (1:1); mp. 153.5° C.;

methyl 1-[2-(4-cyclohexyl-4,5-dihydro-5-oxo-1H-tetrazol-1-yl)ethyl]-4-[(1-oxopropyl)phenylamino]-4-piperidinecarboxylate ethanedioate (1:1); mp. 173° C.;

methyl 1-{2-[4,5-dihydro-5-oxo-4-(2-phenylethyl)-1H-tetrazol-1-yl]ethyl}-4-[(1-oxopropyl)phenylamino]-4-piperidinecarboxylate ethanedioate (2:3); mp. 162.2° C.;

methyl 1-{2-[4,5-dihydro-5-oxo-4-(phenylmethyl)-1H-tetrazol-1-yl]ethyl}-4-[(1-oxopropyl)phenylamino]-4-piperidinecarboxylate ethanedioate (1:1); mp. 191.7° C.;

methyl 1-[2-(4-cyclopropyl)-4,5-dihydro-5-oxo-1H-tet-
razol-1-yl)-ethyl]-4-[(1-oxopropyl)phenylamino]-4-
piperidinecarboxylate ethanedioate (2:3) hemihy-
drate; mp. 155.9° C.; and
methyl 1-[2-(4-ethyl-4,5-dihydro-5-oxo-1H-tetrazol-1-
yl)ethyl]-4-(phenylamino)-4-piperidinecarboxylate
ethanedioate (2:3); mp. 172° C.

EXAMPLE XV

A mixture of 2.55 parts of 1,4-dihydro-1-(2-iodoe-thyl)-4-methyl-5H-tetrazol-5-one, 3.45 parts of N-[4-(methoxymethyl)-4-piperidinyl]-N-phenylpropana-mide, 2 parts of sodium carbonate, 0.2 parts of potassium iodide and 160 parts of 4-methyl-2-pentanone is stirred and refluxed overnight with water-separator. The reaction mixture is cooled, 100 parts of water are added and the layers are separated. The aqueous phase is extracted with dichloromethane. The combined organic phases are dried, filtered and evaporated. The residue is purified by column-chromatography over silica gel using a mixture of trichloromethane and methanol (97:3 by volume) as eluent. The pure fractions are collected and the eluent is evaporated. The residue is converted into the ethanedioate salt in 2-propanone. The salt is filtered off and crystallized from 2-propanone, yielding 2.1 parts (42%) of N-{1-[2-(4,5-dihydro-4-methyl-5-oxo-1H-tetrazol-1-yl)ethyl]-4-(methoxymethyl)-4-piperidinyl}-N-phenylpropanamide ethanedioate (1:1); mp. 155.9° C.

EXAMPLE XVI

Following the procedure of Example XV there is prepared methyl 1-[2-(4,5-dihydro-4-methyl-5-oxo-1H-tetrazol-1-yl)ethyl]-4-[(1-oxopropyl)phenylamino]-4-piperidinecarboxylate ethanedioate (1:1); mp. 185.9° C.; by the reaction of 1,4-dihydro-1-(2-iodoethyl)-4-methyl-5H-tetrazol-5-one with methyl 4-[(1-oxopropyl)-phenylamino]-4-piperidinecarboxylate.

EXAMPLE XVII

A mixture of 3 parts of 1-ethyl-1,4-dihydro-5H-tetrazol-5-one, 9.4 parts of N-[1-(2-chloropropyl)-4-(methoxymethyl)-4-piperidinyl]-N-phenylpropanamide, 2.5 parts of sodium carbonate, 2.5 parts of N,N-diethyle-thanamine and 90 parts of N,N-dimethylformamide is stirred and heated overnight at 70° C. The reaction mixture is cooled, 100 parts of water are added and the product is extracted three times with methylbenzene. The combined extracts are dried, filtered and evaporated. The residue is purified twice by column-chromatography over silica gel using first a mixture of trichloromethane and methanol (97:3 by volume) and then a mixture of ethyl acetate and ethanol (99:1 by volume) as eluent. Two pure fractions are obtained.

The first fraction is evaporated and the residue is converted into the hydrochloride salt in 2-propanone and 2,2'-oxybispropane. The salt is filtered off and dried, yielding 3.9 parts (33.4%) of N-{1-[2-(4-ethyl-4,5-dihydro-5-oxo-1H-tetrazol-1-yl)propyl]-4-(methoxymethyl)-4-piperidinyl}-N-phenylpropanamide monohydrochloride; mp. 192.7° C.

The second fraction is evaporated and the residue is converted into the hydrochloride salt in 2-propanone and 2,2'-oxybispropane. The salt is filtered off and dried, yielding 2.1 parts (18%) of N-{1-[2-(4-ethyl-4,5-dihydro-5-oxo-1H-tetrazol-1-yl)-1-methylethyl]-4-(methoxymethyl)-4-piperidinyl}-N-phenylpropanamide monohydrochloride; mp. 185.4° C.

EXAMPLE XVIII

A mixture of 1.2 parts of 1-ethyl-1,4-dihydro-5H-tetrazol-5-one, 3.9 parts of N-[1-(2-chloropropyl)-4-(methoxymethyl)-4-piperidinyl]-N-phenylpropanamide monohydrochloride, 2 parts of sodium carbonate, 0.1 parts of potassium iodide and 120 parts of 4-methyl-2-pentanone is stirred and refluxed overnight with water-separator. The reaction mixture is cooled, poured onto water and the layers are separated. The organic phase is dried, filtered and evaporated. The residue is purified by column-chromatography over silica gel using a mixture of trichloromethane and methanol (99:1 by volume) as eluent. The pure fractions are collected and the eluent is evaporated. The residue is converted into the nitrate salt in 2-propanone. The salt is filtered off and crystallized twice: first from a mixture of 2,2'-oxybispropane and 2-propanone and then from 2-propanone, yielding 1.5 parts (30%) of N-{1-[2-(4-ethyl-4,5-dihydro-5-oxo-1H-tetrazol-1-yl)-1-methylethyl]-4-(methoxymethyl)-4-piperidinyl}-N-phenylpropanamide mononitrate; mp. 146.6° C.

EXAMPLE XIX

Following the procedure of Example XVIII there is prepared N-{1-[2-(4,5-dihydro-5-oxo-4-phenyl-1H-tetrazol-1-yl)-1-methylethyl]-4-(methoxymethyl)-4-piperidinyl}-N-phenylpropanamide mononitrate; mp. 151.2° C.; by the reaction of 1,4-dihydro-1-phenyl-5H-tetrazol-5-one with N-[1-(2-chloropropyl)-4-(methoxymethyl)-4-piperidinyl]-N-phenylpropanamide monohydrochloride.

EXAMPLE XX

A mixture of 3 parts of 1-ethyl-1,4-dihydro-5H-tetrazol-5-one, 8 parts of N-[1-(2-chloro-2-phenylethyl)-4-(methoxymethyl)-4-piperidinyl]-N-phenylpropanamide, 0.2 parts of potassium iodide, 5 parts of sodium carbonate and 135 parts of N,N-dimethylformamide is stirred and heated overnight at 70° C. The reaction mixture is cooled to room temperature and 150 parts of water are added. The product is extracted three times with methylbenzene. The combined extracts are dried, filtered and evaporated. The solid residue is purified by column-chromatography over silica gel using a mixture of trichloromethane and methanol (97:3 by volume) as eluent. The pure fractions are collected and the eluent is evaporated. The residue is crystallized from a mixture of petroleum-ether and 2,2'-oxybispropane. The product is filtered off and dried, yielding 5.7 parts (65%) of N-{1-[2-(4-ethyl-4,5-dihydro-5-oxo-1H-tetrazol-1-yl)-2-phenylethyl]-4-(methoxymethyl)-4-piperidinyl}-N-phenylpropanamide; mp. 125.7° C.

EXAMPLE XXI

A mixture of 5.7 parts of methyl 1-[2-(4-ethyl-4,5-dihydro-5-oxo-1H-tetrazol-1-yl)ethyl]-4-(phenylamino)-4-piperidinecarboxylate, 1.9 parts of cyclopropanecarbonyl chloride, 2.7 parts of N,N-diethylethanamine and 68 parts of methylbenzene is stirred and refluxed overnight. The reaction mixture is cooled, 100 parts of water are added and the layers are separated. The organic phase is dried, filtered and evaporated. The residue is purified by column-chromatography over silica gel using a mixture of trichloromethane and methanol (98:2 by volume) as eluent. The pure fractions are collected and treated with 1 part of ethanedioic acid. The formed ethanedioate salt is filtered off and crystallized from a mixture of 2-propanone and 2,2'-oxybispropane, yielding 1.5 parts (17.5%) of methyl 4-[(cyclopropylcarbonyl)phenylamino]-1-[2-(4-ethyl-4,5-dihydro-5-oxo-1H-tetrazol-1-yl)ethyl]-4-piperidinecarboxylate ethanedioate (2:3); mp. 181.5° C.

EXAMPLE XXII

Following the procedure of Example V and using equivalent amounts of the appropriate starting materials there are obtained:

1-(2-chloro-1-methylpropyl)-1,4-dihydro-4-ethyl-5H-tetrazol-5-one;
1-(3-chloro-1-methylbutyl)-1,4-dihydro-4-ethyl-5H-tetrazol-5-one;
1-(2-chloro-1-methylpropyl)-1,4-dihydro-4-methyl-5H-tetrazol-5-one;
1-(3-chloro-1-methylbutyl)-1,4-dihydro-4-propyl-5H-tetrazol-5-one;
1-(3-chloro-1-phenylpropyl)-1,4-dihydro-4-ethyl-5H-tetrazol-5-one; and
1-(3-chloro-3-methyl-1-phenylpropyl)-1,4-dihydro-4-ethyl-5H-tetrazol-5-one.

EXAMPLE XXIII

Following the procedures described herein and using appropriate starting materials the following compounds of formula I can still be prepared:

EXAMPLE XXIV

Following the procedure of Example IX and using equivalent amounts of the appropriate starting materials there is also obtained:

N-[1-(2-chloro-1-methyl-2-phenylethyl)-4-piperidinyl]-N-phenylpropanamide.

EXAMPLE XXV

Following the procedure of Example XX and using equivalent amounts of the appropriate starting materials there is also obtained:

N-{1-[2-(4-ethyl-4,5-dihydro-5-oxo-1H-tetrazol-1-yl)-1-methyl-2-phenylethyl]-4-(methoxymethyl)-4-piperidinyl}-N-phenylpropanamide.

I claim:

1. A chemical compound selected from the group consisting of a N-phenyl-N-(4-piperidinyl)amide derivative having the formula:

| R | Z | n | $R^1$ | $R^2$ | $R^3$ | $R^4$ | $R^5$ | $R^6$ |
|---|---|---|---|---|---|---|---|---|
| H | O | 0 | H | H | $COOCH_3$ | $C_2H_5$ | H | H |
| H | S | 1 | H | H | $COOCH_3$ | $C_2H_5$ | H | H |
| H | O | 0 | H | H | $CH_2OCH_3$ | $CH_3$ | 3-$CH_3$ | H |
| H | O | 0 | H | H | $COOC_2H_5$ | $C_2H_5$ | H | H |
| cyclopropyl | O | 0 | H | H | $COOC_2H_5$ | $C_2H_5$ | H | H |
| $CH_2=CH-CH_2$ | O | 0 | H | H | $COOC_2H_5$ | $C_2H_5$ | H | H |
| $CH_2=CH-CH_2$ | O | 0 | H | H | $COCH_3$ | $C_2H_5$ | H | H |
| $CH\equiv C-CH_2$ | O | 0 | H | H | $COOC_2H_5$ | $C_2H_5$ | H | H |
| $C_2H_5O-CH_2CH_2$ | O | 0 | H | H | $COOC_2H_5$ | $C_2H_5$ | H | H |
| 4-Cl—$C_6H_4$ | O | 0 | H | H | $COCH_3$ | $C_2H_5$ | H | H |
| 2-F—$C_6H_4$ | O | 0 | H | H | $COCH_3$ | $C_2H_5$ | 3-$CH_3$ | 4-Cl |
| 4-$CH_3$—$C_6H_4$ | O | 0 | H | H | $COOCH_3$ | $C_3H_7$ | H | 4-Cl |
| 2,4-$(CH_3O)_2$—$C_6H_3$ | O | 0 | H | H | $CH_2OCH_3$ | $C_2H_5$ | H | 4-F |
| 3-$(CF_3)$—$C_6H_4$ | O | 0 | H | H | $COOC_2H_5$ | $CH_3$ | 3-$CH_3$ | 3-$CF_3$ |
| 4-Cl—$C_6H_4$—$CH_2$ | O | 0 | H | H | $COOCH_3$ | cyclopropyl | H | H |
| 2-(thienyl)ethyl | O | 0 | H | H | $COOCH_3$ | $CH_2-CH=CH_2$ | H | H |
| 2-(pyridinyl)ethyl | O | 0 | H | H | $COCH_3$ | $OC_2H_5$ | H | 4-$CH_3$ |
| $C_2H_5$ | S | 1 | H | H | $COOCH_3$ | $CH_2-C_6H_5$ | H | 4-$OCH_3$ |
| $C_2H_5$ | O | 0 | $CH_3$ | $CH_3$ | $COOCH_3$ | $C_2H_5$ | H | H |
| $C_2H_5$ | O | 1 | $CH_3$ | $CH_3$ | $COOCH_3$ | $C_2H_5$ | H | H |
| $CH_3$ | O | 0 | $CH_3$ | $CH_3$ | $COOCH_3$ | $C_2H_5$ | H | H |
| $nC_3H_7$ | O | 1 | $CH_3$ | $CH_3$ | $COOCH_3$ | $C_2H_5$ | H | H |
| $C_2H_5$ | O | 0 | $CH_3$ | $CH_3$ | $COCH_3$ | $C_2H_5$ | H | H |
| $C_2H_5$ | O | 1 | $CH_3$ | $CH_3$ | $COCH_3$ | $C_2H_5$ | H | H |
| $CH_3$ | O | 0 | $CH_3$ | $CH_3$ | $COCH_3$ | $C_2H_5$ | H | H |
| $nC_3H_7$ | O | 1 | $CH_3$ | $CH_3$ | $COCH_3$ | $C_2H_5$ | H | H |
| $C_2H_5$ | O | 0 | $CH_3$ | $CH_3$ | $CH_2OCH_3$ | $C_2H_5$ | H | H |
| $C_2H_5$ | O | 1 | $CH_3$ | $CH_3$ | $CH_2OCH_3$ | $C_2H_5$ | H | H |
| $CH_3$ | O | 0 | $CH_3$ | $CH_3$ | $CH_2OCH_3$ | $C_2H_5$ | H | H |
| $nC_3H_7$ | O | 1 | $CH_3$ | $CH_3$ | $CH_2OCH_3$ | $C_2H_5$ | H | H |
| $C_2H_5$ | O | 1 | $C_6H_5$ | H | $COOCH_3$ | $C_2H_5$ | H | H |
| $C_2H_5$ | O | 1 | $C_6H_5$ | $CH_3$ | $COOCH_3$ | $C_2H_5$ | H | H |
| $C_2H_5$ | O | 1 | $C_6H_5$ | H | $COCH_3$ | $C_2H_5$ | H | H |
| $C_2H_5$ | O | 1 | $C_6H_5$ | $CH_3$ | $COCH_3$ | $C_2H_5$ | H | H |
| $C_2H_5$ | O | 1 | $C_6H_5$ | H | $CH_2OCH_3$ | $C_2H_5$ | H | H |
| $C_2H_5$ | O | 1 | $C_6H_5$ | $CH_3$ | $CH_2OCH_3$ | $C_2H_5$ | H | H |

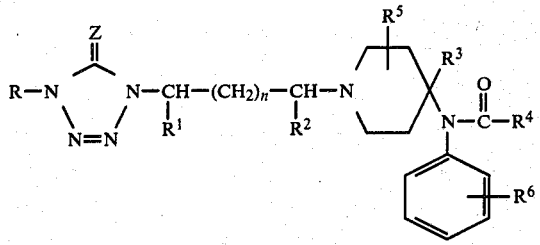

and the pharmaceutically acceptable acid addition salts thereof,
wherein:
R is a member selected from the group consisting of hydrogen, lower alkyl, cycloalkyl, having 3 to 6 ring carbon atoms lower alkenyl, lower alkynyl, (lower alkyl)oxy(lower alkyl), aryl and aryl(lower alkyl);
$R^1$ is a member selected from the group consisting of hydrogen, lower alkyl and aryl;
$R^2$ is a member selected from the group consisting of hydrogen and lower alkyl;
$R^3$ is a member selected from the group consisting of lower alkyloxycarbonyl, lower alkyloxymethyl and lower alkylcarbonyl;
$R^4$ is a member selected from the group consisting of lower alkyl, cycloalkyl, having 3 to 6 ring carbon atoms lower alkenyl, lower alkyloxy and arylmethyl;
$R^5$ is a member selected from the group consisting of hydrogen and lower alkyl;
$R^6$ is a member selected from the group consisting of hydrogen, halo, lower alkyl, lower alkyloxy and trifluoromethyl;
Z is a member selected from the group consisting of O and S; and
n is the integer 0 or 1;
wherein said aryl as used in the foregoing definitions is selected from the group consisting of phenyl, substituted phenyl, thienyl and pyridinyl, said substituted phenyl having from 1 to 2 substituents independently selected from the group consisting of halo, lower alkyl, lower alkyloxy, and trifluoromthyl.

2. A chemical compound selected from the group consisting of N-{1-[2-(4-ethyl-4,5-dihydro-5-oxo-1H-tetrazol-1-yl)ethyl]-4-(methoxymethyl)-4-piperidinyl}-N-phenylpropanamide and the pharmaceutically acceptable acid addition salts thereof.

3. A chemical compound selected from the group consisting of methyl 1-[2-(4,5-dihydro-4-methyl-5-oxo-1H-tetrazol-1-yl)ethyl]-4-[(1-oxopropyl)phenylamino]-4-piperidinecarboxylate and the pharmaceutically acceptable acid addition salts thereof.

4. A chemical compound selected from the group consisting of methyl 1-[2-(4-ethyl-4,5-dihydro-5-oxo-1H-tetrazol-1-yl)ethyl]-4-[(1-oxopropyl)methylamino]-4-piperidinecarboxylate and the pharmaceutically acceptable acid addition salts thereof.

5. A chemical compound selected from the group consisting of methyl 1-[2-(4,5-dihydro-5-oxo-4-propyl-1H-tetrazol-1-yl)ethyl]-4-[(1-oxopropyl)phenylamino]-4-piperidinecarboxylate and the pharmaceutically acceptable acid addition salts thereof.

6. A chemical compound selected from the group consisting of N-{1-[2-(4,5-dihydro-4-methyl-5-oxo-1H-tetrazol-1-yl)ethyl]-4-(methoxymethyl)-4-piperidinyl}-N-phenylpropanamide and the pharmaceutically acceptable acid addition salts thereof.

7. A chemical compound selected from the group consisting of N-{1-[2-(4-ethyl-4,5-dihydro-5-oxo-1H-tetrazol-1-yl)-1-methylethyl]-4-(methoxymethyl)-4-piperidinyl}-N-phenylpropanamide and the pharmaceutically acceptable acid addition salts thereof.

8. A pharmaceutical composition comprising an inert carrier material and as an active ingredient an effective analgesic amount of a compound selected from the group consisting of a N-phenyl-N-(4-piperidinyl)amide derivative having the formula:

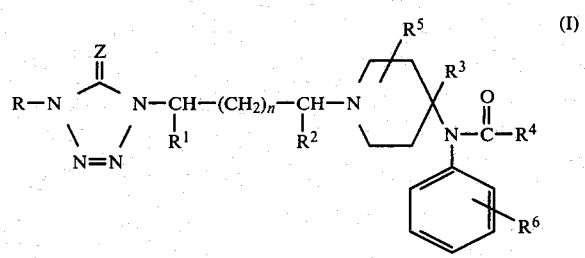

and the pharmaceutically acceptable acid addition salts thereof, wherein:
R is a member selected from the group consisting of hydrogen, lower alkyl, cycloalkyl, having 3 to 6 ring carbon atoms lower alkenyl, lower alkynyl, (lower alkyl)oxy(lower alkyl), aryl and aryl(lower alkyl);
$R^1$ is a member selected from the group consisting of hydrogen, lower alkyl and aryl;
$R^2$ is a member selected from the group consisting of hydrogen and lower alkyl;
$R^3$ is a member selected from the group consisting of lower alkyloxycarbonyl, lower alkyloxymethyl and lower alkylcarbonyl;
$R^4$ is a member selected from the group consisting of lower alkyl, cycloalkyl, having 3 to 6 ring carbon atoms lower alkenyl, lower alkyloxy and arylmethyl;
$R^5$ is a member selected from the group consisting of hydrogen and lower alkyl;
$R^6$ is a member selected from the group consisting of hydrogen, halo, lower alkyl, lower alkyloxy and trifluoromethyl;
Z is a member selected from the group consisting of O and S; and
n is the integer 0 or 1;
wherein said aryl as used in the foregoing definitions is selected from the group consisting of phenyl, substituted phenyl, thienyl and pyridinyl, said substituted phenyl having from 1 to 2 substituents independently selected from the group consisting of halo, lower alkyl, lower alkyloxy, and trifluoromethyl.

9. A pharmaceutical composition comprising an inert carrier material and as an active ingredient an effective analgesic amount of a compound selected from the group consisting of N-{1-[2-(4-ethyl-4,5-dihydro-5-oxo-1H-tetrazol-1-yl)ethyl]-4-(methoxymethyl)-4-piperidinyl}-N-phenylpropanamide and the pharmaceutically acceptable acid addition salts thereof.

10. A pharmaceutical composition comprising an inert carrier material and as an active ingredient an effective analgesic amount of a compound selected from the group consisting of methyl 1-[2-(4,5-dihydro-4-methyl-5-oxo-1H-tetrazol-1-yl)ethyl]-4-[(1-oxopropyl)phenylamino]-4-piperidinecarboxylate and the pharmaceutically acceptable acid addition salts thereof.

11. A pharmaceutical composition comprising an inert carrier material and as an active ingredient an effective analgesic amount of a compound selected from the group consisting of methyl 1-[2-(4-ethyl-4,5-dihydro-5-oxo-1H-tetrazol-1-yl)ethyl]-4-[(1-oxopropyl)phenylamino]-4-piperidinecarboxylate and the pharmaceutically acceptable acid addition salts thereof.

12. A pharmaceutical composition comprising an inert carrier material and as an active ingredient an effective analgesic amount of a compound selected from the group consisting of methyl 1-[2-(4,5-dihydro-5-oxo-4-propyl-1H-tetrazol-1-yl)ethyl]-4-[(1-oxopropyl)phenylamino]-4-piperidinecarboxylate and the pharmaceutically acceptable acid addition salts thereof.

13. A pharmaceutical composition comprising an inert carrier material and as an active ingredient an effective analgesic amount of a compound selected from the group consisting of N-{1-[2-(4,5-dihydro-4-methyl-5-oxo-1H-tetrazol-1-yl)ethyl]-4-(methoxymethyl)-4-piperidinyl}-N-phenylpropanamide and the pharmaceutically acceptable acid addition salts thereof.

14. A pharmaceutical composition comprising an inert carrier material and as an active ingredient an effective analgesic amount of a compound selected from the group consisting of N-{1-[2-(4-ethyl-4,5-dihydro-5-oxo-1H-tetrazol-1-yl)-methylethyl]-4-(methoxymethyl)-4-piperidinyl}-N-phenylpropanamide and the pharmaceutically acceptable acid addition salts thereof.

* * * * *

UNITED STATES PATENT AND TRADEMARK OFFICE

CERTIFICATE EXTENDING PATENT TERM
UNDER 35 U.S.C. 156

Patent No.     : 4,167,574

Dated          : September 11, 1979

Inventor(s)    : Frans Janssens

Patent Owner   : Janssen Pharmaceutica, N.V.

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

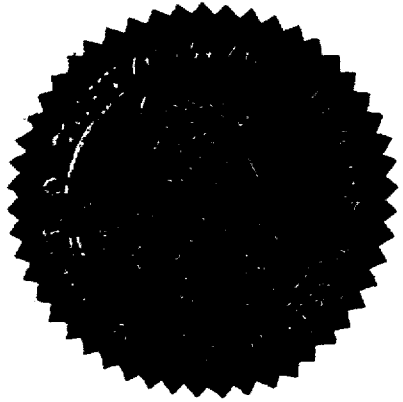

I have caused the seal of the Patent and Trademark Office to be affixed this Twenty-second day of December 1987.

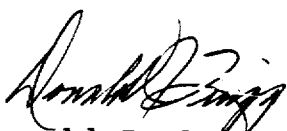

Donald J. Quigg

Assistant Secretary and Commissioner of Patents and Trademarks